(12) United States Patent
Schnell

(10) Patent No.: US 8,474,459 B2
(45) Date of Patent: Jul. 2, 2013

(54) DEVICE FOR INTRODUCING A TRACHEAL CANNULA INTO A TRACHEOSTOMA

(75) Inventor: Ralf Schnell, Seligenstadt (DE)

(73) Assignee: Tracoe Medical GmbH, Frankfurt am Main, DE (US)

( * ) Notice: Subject to any disclaimer, the term of this patent is extended or adjusted under 35 U.S.C. 154(b) by 850 days.

(21) Appl. No.: 12/305,430

(22) PCT Filed: Jun. 22, 2007

(86) PCT No.: PCT/EP2007/056262
§ 371 (c)(1),
(2), (4) Date: Dec. 18, 2008

(87) PCT Pub. No.: WO2008/000701
PCT Pub. Date: Jan. 3, 2008

(65) Prior Publication Data
US 2009/0178674 A1    Jul. 16, 2009

(30) Foreign Application Priority Data
Jun. 26, 2006  (DE) .......................... 10 2006 029 599

(51) Int. Cl.
*A61M 16/00* (2006.01)
*A61M 37/00* (2006.01)
*A62B 9/06* (2006.01)
*A61F 11/00* (2006.01)

(52) U.S. Cl.
USPC ................. 128/207.14; 128/207.15; 606/108; 604/23

(58) Field of Classification Search
USPC ............. 128/207.15, 207.14, 207.17, 207.29; 604/170, 119, 100, 165, 166, 24, 25, 27; 606/108; 600/114, 120, 121, 129
See application file for complete search history.

(56) References Cited

U.S. PATENT DOCUMENTS

| | | | | |
|---|---|---|---|---|
| 4,351,330 A * | 9/1982 | Scarberry | ............... | 128/207.15 |
| 4,502,482 A * | 3/1985 | DeLuccia et al. | ........ | 128/207.15 |
| 4,637,388 A | 1/1987 | Melendy | | |
| 4,762,125 A * | 8/1988 | Leiman et al. | ........... | 128/207.15 |
| 4,846,804 A * | 7/1989 | Davis et al. | .............. | 604/170.02 |
| 4,913,139 A * | 4/1990 | Ballew | ...................... | 128/200.11 |
| 4,978,334 A | 12/1990 | Toye et al. | | |
| 5,058,580 A * | 10/1991 | Hazard | ...................... | 128/207.15 |
| 5,188,100 A * | 2/1993 | Miles et al. | ............... | 128/207.14 |
| 5,653,230 A * | 8/1997 | Ciaglia et al. | ............. | 128/207.15 |
| 6,039,722 A * | 3/2000 | Greive | .......................... | 604/528 |
| 6,228,068 B1 * | 5/2001 | Yoon | ............................. | 604/246 |
| 2008/0142005 A1 | 6/2008 | Schnell | | |

* cited by examiner

*Primary Examiner* — Loan Thanh
*Assistant Examiner* — Sundhara Ganesan
(74) *Attorney, Agent, or Firm* — Paul & Paul

(57) ABSTRACT

The present invention concerns a device having a guide catheter for the introduction of a tracheal cannula into a tracheostoma. To provide a device for introducing a tracheal cannula into a tracheostoma, which prevents injury by the distal end face of the cannula and which is suitable for use in relation to highly flexible cannulas, in relation to cannulas of tight inside diameter and/or of large wall thickness, it is proposed in accordance with the invention that the guide catheter has a shield which is mounted in the proximity of the distal end of the guide catheter and which comprises a flexible material and which is substantially in the form of a distally directed conical tip, wherein the tube of the guide catheter passes through the axis of said tip, with a base outside diameter which in a first state corresponds at least to the outside diameter of the tracheal cannula and in a second state by deformation is smaller than the inside diameter of the tracheal cannula and is thus retractable through the tracheal cannula.

20 Claims, 3 Drawing Sheets

DEVICE FOR INTRODUCING A TRACHEAL CANNULA INTO A TRACHEOSTOMA

The present invention concerns a device having a guide catheter for introducing a tracheal cannula into a tracheostoma with a guide catheter.

The method of tracheotomy is used both in emergency medicine and also in long-term artificial respiration. As an alternative to the classic operative procedure, various percutaneous tracheotomy procedures, in particular percutaneous dilation tracheotomy, have also been developed within the last decades.

In percutaneous dilation tracheotomy in accordance with Ciaglia or Griggs or Frova, a guide wire is firstly introduced into the trachea by way of an aspiration needle. After dilation with a 14 French dilator the guide wire can be reinforced by pulling a guide catheter thereover. The unit of the guide wire and the guide catheter then serves as a guide rail for dilation of the tracheal aspiration passage by means of a curved conical dilator, forceps or a screw-shaped dilator. After appropriate expansion of the aspiration passage and subsequent removal of the dilator the tracheotomy cannula can be introduced in a similar fashion using the guide wire and the guide catheter as a guide rail by means of an insertion aid provided for that purpose. A similar procedure can be adopted when changing the cannula, in which case it is possible to dispense with a guide wire.

In that respect insertion of the tracheotomy cannula after removal of the dilator should be effected very rapidly as the patient is generally not given artificial respiration during that time. In addition there is the risk of a hemorrhage as the pressure on the enlarged stoma is reduced during the removal of the dilator. A further problem is that the stoma contracts again after dilation is effected. To compensate for that the stoma is generally expanded noticeably more in dilation than the outside diameter of the tracheal cannula would require. That substantial dilation increases the risk of tracheal ring fractures.

In order to be able to introduce the tracheotomy cannula into the tracheostoma which is very tightly applied in percutaneous dilation tracheotomy, use is made of an insertion aid, the maximum outside diameter of which is slightly smaller than the inside diameter of the cannula and the tip of which is conically tapered similarly to the dilators at the distal end (patient end) and which is introduced into the cannula from the proximal end (physician end). In that case however there is a step-shaped sudden change in calibre at the transition between the insertion aid which protrudes from the distal end of the cannula, and the outside diameter at the end of the cannula wall. In cannulas of thick walls that abrupt transition can represent a serious problem. In the attempt to insert the cannula the end wall of the cannula frequently remains caught on one of the tracheal rings. In that case fracture of cartilage rings or injury to the rear wall of the trachea can occur. Some manufacturers of tracheotomy cannulas have tried to resolve that problem by tapering the end wall of the cannula conically inwardly. That admittedly helps with insertion, but there are sharp edges at the end of the cannula, which can cause problems when carrying the cannulas.

DE 10 2005 021 470 which has not yet been published, to resolve that problem, describes an insertion aid having a conical tip which in one state at least partially covers the distal end of the tracheal cannula but which in another state is of a smaller base diameter so that the insertion aid in that state can be retracted through the tracheal cannula. That invention has proven to be highly successful for cannulas of a thin wall thickness (0.8 mm) and of an inside diameter for the tracheotomy cannula of at least 8 mm. The wall thickness of most cannulas however is markedly above 0.8 mm and to compensate for that change in calibre, insertion aids having a conical tip of correspondingly great wall thickness are required. For steric reasons however they can only still be pushed with difficulty through the tracheotomy cannula in the direction of the cannula tip. The softer the cannula tube is, the greater the problems involved in pushing the insertion aid with the conical tip through the cannula tube in the direction of the distal end as the conical tip easily becomes wedged tight in the tube. Retraction also becomes more difficult as a result.

A further problem is that the relationship between the free cross-sectional area and the wall thickness of the conical tip becomes very detrimental if the inside diameter of a tracheotomy cannula is less than 8 mm and the conical tip can thereby only be brought into the state involving a small base diameter, with very great difficulty.

In addition, with known tracheal cannulas with insertion aids, there is the problem that the insertion aid can only be retracted with difficulty after insertion of the tracheal cannula into the trachea of the patient. That is the case in particular if there is very little play between the insertion aid and the tracheal cannula. Removal of the insertion aid is also possible only with the application of a considerable amount of force, in the case of commercially available soft cannulas of silicone or PVC and in the case of cannulas, the bend of which is such that the insertion aid has to be deformed during retraction. That problem can admittedly be reduced by the use of lubricants, but there is the danger that the treating physician by mistake misses out that working step.

Taking that state of the art as its basic starting point, the object of the present invention is to provide a device for introducing a tracheal cannula into a tracheostoma, which prevents injury due to the distal end face of the cannula and which is suitable for use in relation to highly flexible cannulas, in relation to cannulas of a tight inside diameter and/or of large wall thickness. Preferably the invention seeks to provide a device with which it is also possible to effect dilation of the stoma and introduction of the tracheal cannula in one step.

That object is attained in that the guide catheter has a shield which is mounted to the guide catheter in the proximity of the distal end of the guide catheter and which comprises a flexible material and which is substantially in the form of a distally directed conical tip, wherein the tube of the guide catheter passes through the axis of said tip, with a base outside diameter which in a first state approximately corresponds to the outside diameter of the tracheal cannula and in a second state by deformation is smaller than the inside diameter of the tracheal cannula and is thus retractable through the tracheal cannula.

In that respect the first and second states are to be selectively adjustable.

The term 'conical' is not to be interpreted in the strictly geometrical sense but relates essentially to a diameter which increases from the tip towards the base without an abrupt enlargement, wherein the contour of the 'cone' can also be concavely or convexly curved.

The term 'base' denotes the plane of the shield perpendicularly to its axis, which is of the largest diameter.

In that respect the term 'distal' denotes the end towards the patient, that is to say the end which is introduced into the patient, in contrast to 'proximal', which denotes the end towards the physician.

It will be appreciated that in that respect the shield is arranged on the catheter in such a way that, during insertion of the catheter into the tracheostoma, with or without the cannula, the tip of the shield points in the direction of the distal end of the catheter and the base is correspondingly proximally disposed.

An advantage of the device according to the invention is that the distal end face of the cannula wall is completely covered by the shield and as a result injury when introducing the cannula can be avoided. Before using this device the guide catheter is inserted with the shield from the distal end into the tracheal cannula. The shield can thereby be optimally placed and only has to be retracted through the cannula after insertion of the tracheal cannula into the trachea of the patient. It is possible to fit the shield to any catheter suitable for that purpose. In that respect the distal end of the guide catheter should be as soft as possible and rounded to obviate injuries.

In that respect the change in the state of the shield is preferably effected by specifically targeted relative movement between the guide catheter and the cannula, that is to say for example by holding fast the inserted cannula and withdrawing the guide catheter.

It will be appreciated that the device according to the invention can also be employed when inserting other tubes into artificial or natural body openings, for example when introducing endotracheal tubes.

After pre-dilation has been effected (for example with a conventional 14 French dilator), dilation and insertion of the tracheal cannula can be effected in one step by means of the device according to the invention. It will be appreciated that it is also possible to use the device after dilation with commercially available dilators.

The device according to the invention further has the advantage that the guide catheter cannot slip from the distal end into the insertion aid or the dilator, by virtue of the shield fixed thereto. That additionally reduces the risk of injury as in those cases there would be the possibility that the unprotected guide wire could snap off and thus the insertion aid or the dilator could injure the rear wall of the trachea.

It is preferred for that purpose for the outside base diameter of the shield in the first state to correspond to the outside diameter of the tracheal cannula, but a deviation (in particular a reduction) in the base diameter in relation to the outside diameter of the cannula by about 50% of the wall thickness of the tracheal cannula can be tolerated, in particular if the end of the cannula is rounded.

In a preferred embodiment the shield in the first state is substantially in the form of a hollow cone and is shaped conically on the inside and the outside. Shaping the shield in the form of a hollow cone has the advantage that there are various possible ways of implementing deformation, by which the shield can be put into the second state. It is possible for the smaller base outside diameter to be achieved by indentation of the hollow cone wall, similarly to collapsing an umbrella. It is preferable however for the shield to be such that it is partially or entirely folded over from the tip to adopt the second state.

It is advantageous if the shield is of a maximum wall thickness at the base of at most 2.5 mm, preferably at most 1.5 mm and at least 0.4 mm, preferably at least 0.5 mm. Those wall thicknesses are thick enough to withstand the pressure which loads the shield upon introduction of the cannula into the tracheostoma. The wall thicknesses however are also thin enough so that the shield can be put into the second state and can thereby be retracted through the tracheal cannula without any problem. Preferably the wall of the shield tapers from the base to the tip. That provides for sufficient stabilisation upon introduction of the tracheal cannula with at the same time retractability of the shield through the cannula.

In a preferred embodiment of the invention the base of the shield is at a spacing of a minimum of 2, better from 5 to 14 cm, preferably from 7 to 10 cm, from the distal end of the guide catheter. Upon insertion of the cannula firstly a guide wire is introduced into the tracheostoma, over which the guide catheter is then inserted. That guide catheter serves as a guide for the subsequent introduction of the tracheal cannula, it must therefore project sufficiently far into the trachea. A distal end of the guide catheter which protrudes excessively from the tracheal cannula could on the other hand lead to injury to the trachea.

Preferably the axial length of the shield is between 1 cm and 6 cm, particularly preferably between 1.5 cm and 3 cm. A shield of a greater axial length could only be retracted through the cannula with very great difficulty or not at all, for steric reasons. In order however to permit insertion as gently and carefully as possible and to expand the stoma only slowly, the shield should be of a minimum length of 1 cm.

It is also preferable if the cone angle between the shield and the longitudinal axis of the guide catheter is between 3° and 30°, preferably between 5° and 15°. Shields with a particularly small cone angle provide for particularly gentle insertion into the trachea and slow dilation of the stoma. An excessively small angle however, with given minimum diameters of cannulas, would inevitably lead to very long shields which would be more difficult to handle.

A particular embodiment provides that a displacement body in the form of a hollow cylinder, the outside diameter of which is smaller than the inside diameter of the cannula and which can be pushed on in the cannula over the guide catheter, is in engagement with an inside surface of the shield in the first state. That displacement body serves for stabilisation of the shield. When using the displacement body a greater pressure can be exerted on the trachea by way of the shield without the shield noticeably deforming or folding over, which facilitates expansion of the stoma. The displacement body can be retracted after introduction of the tracheal cannula independently from the guide catheter, whereby the guide catheter has more clearance in the cannula and retraction of the guide catheter with the deformed shield is simplified.

There is however also the possibility of designing the displacement body in such a way that it substantially comprises a short hollow cylinder, the diameter of which is less small than the inside diameter of the cannula and which, after being pushed in, comes to lie in the distal end of the cannula, which is adjoined by a flexible tubular attachment which is longer than the cannula and which serves for insertion and removal of the displacement body.

A preferred embodiment is also one in which the outside diameter of the displacement body is at least 0.2 mm, preferably at least 1 mm and at most 4 mm, preferably at most 1.5 mm smaller than the inside diameter of the tracheal cannula. The displacement body is generally pushed in from the proximal end of the tracheal cannula. If its outside diameter is smaller than the inside diameter of the tracheal cannula it is thus easier for it to be pushed in, even in relation to cannulas having highly flexible walls or of very small inside diameter. If the diameter of the displacement body is excessively small it can no longer sufficiently support the shield upon insertion of the tracheal cannula.

A particularly preferred embodiment is one in which the base of the shield has an attachment in the form of a hollow cylinder, of an outside diameter which is adapted to the inside diameter of the cannula and which is greater or smaller than same by a maximum of 10%, preferably a maximum of 5%, with respect to the inside diameter, and of a wall thickness which is between 0.5 mm and 2 mm, preferably between 0.5 mm and 1 mm. That attachment results in a step between the base of the conical tip and the attachment in the form of a hollow cylinder of the shield. The radial depth of that step in the first state substantially corresponds to the thickness of the cannula tube. Upon insertion of the guide catheter with the shield from the distal end into the cannula the attachment is pushed into the cannula tube while the base of the shield comes to bear against the distal end face of the cannula tube. That embodiment affords improved stability for the shield so that it is not by mistake folded over or collapsed upon pressure applied in the direction of the cannula tube. Displacement of the insertion aid relative to the longitudinal axis of the cannula is also prevented thereby, thereby permitting the physician to provide for more controlled insertion or dilation.

When using a displacement body it is desirable if the cylindrical attachment at the base of the shield is of an outside diameter which is adapted to the inside diameter of the cannula and is larger or smaller than same by a maximum of 10%, preferably a maximum of 5%, with respect to the inside diameter, and is of an inside diameter which substantially corresponds to the outside diameter of the displacement body or is somewhat smaller. As a result the cylindrical attachment in the first state of the shield is disposed between the cannula tube and the displacement body. In that respect, for pushing the shield on to the displacement body, it is advantageous if the hollow-cylindrical attachment tapers in the proximal direction.

A preferred device is also one in which the axial length of the hollow-cylindrical attachment at the base of the shield is between 0.3 and 5 mm, preferably between 1 and 3 mm. For optimum stabilisation to prevent the shield from collapsing during penetration of the cannula the hollow-cylindrical attachment must be sufficiently long. In contrast an excessively long attachment could be an impediment in deformation of the shield or could possibly entirely prevent such deformation.

Another preferred embodiment is one in which the displacement body has a conical tip at its distal end. It is desirable if that tip is of a complementary configuration to a conical inside surface of the shield. That provides that the shield is particularly well stabilised upon introduction of the cannula.

Particularly preferably the shield comprises a substantially elastic material. If such an elastic shield is used together with a displacement body the shield should be of an inside diameter which is less than the outside diameter of the displacement body by 0-40%, preferably 20-30%, with respect to the outside diameter of the displacement body. That affords the possibility that the shield can be stressed by way of the tip of the displacement body, which enhances the stability and the hold of the shield and the displacement body, particularly if a shield having a hollow-cylindrical attachment at the base is used. When using an elastic shield in the device according to the invention the second state of the shield can correspond to the unstressed state thereof. Such a shield can be retracted through the tracheal cannula without being folded inside out.

A further preferred configuration of the invention is one in which the shield and/or the displacement body is of a substantially oval cross-section. In that case the shield and/or the displacement body should be so oriented that the extent thereof perpendicularly to the tracheal rings of the patient is smaller than in the direction in which the tracheal rings extend. That can be achieved for example solely or predominantly by a wall thickness which is reduced perpendicularly to the tracheal rings or increased parallel to the tracheal rings, in which case the difference in the wall thicknesses can be for example between 0.25 mm and 1 mm. As expansion of the stoma perpendicularly to the tracheal rings is more difficult than between the rings, that embodiment can be more easily inserted into the stoma or can cause easier dilation of the stoma. A further advantage of this embodiment is that the tracheal cannula which is generally of a round cross-section can be expanded by an oval shield and/or oval displacement body in the direction of the tracheal rings and/or can be reduced perpendicularly thereto. That oval deformation facilitates insertion of the cannula into the trachea, as explained above. That is achieved in particular when the displacement body is of an oval cross-section. When the displacement body is removed the tracheal cannula resumes its original round cross-section. The same effect can be achieved by a displacement body which is of an oval shape at least at the distal end.

A particularly preferred embodiment is one in which the displacement body is a conventional insertion aid. The insertion aids which are known from the state of the art and in which a step occurs between the insertion aid and the distal end of the cannula represent a specific configuration of a displacement body. The use of such conventional insertion aids reduces the costs of manufacture of the device according to the invention as it is possible to use cannulas already on the market with an insertion aid and it is only necessary for a guide catheter with the shield according to the invention to replace the conventional catheter.

Preferably the shield comprises an elastic material such as silicone, a thermoplastic elastomer (TPE), latex or polyurethane. Those materials are suitable for producing a sufficiently flexible and possibly elastic shield which at the same time has the necessary stability. Moreover those materials can be treated in accordance with the requirements in the medical field so that they are sterile.

A preferred embodiment is also one in which the shield is provided with a hydrophilic coating. Such a coating preferably has a low coefficient of friction after moistening and thereby facilitates insertion of the cannula. It will be appreciated that it is sufficient if the outside surface of the shield is covered with such a coating. As an alternative thereto the shield can also be wetted with lubricant gel on its outside surface, that has the same function as the above-described coating.

A further preferred embodiment is one in which the tip of the shield has an attachment in the form of a hollow cylinder. That attachment serves substantially for fixing the shield to the guide catheter. In turn it can have a conical tip so that there is no sudden change in calibre between the guide catheter and that distal attachment. It is particularly advantageous if the conical tip represents a prolongation of the shield and in that way the outside surfaces of the tip and the shield form a continuous surface without a pronounced transition.

A particularly preferred embodiment is one in which the shield is joined to the guide catheter by adhesive or welding. That kind of fixing is sufficiently strong to prevent detachment of the shield from the guide catheter for example during retraction. The guide catheter could also be produced in one piece with the shield, for example by injection moulding.

Further advantages, features and possible uses of the present invention will be apparent from the description hereinafter of preferred embodiments and the Figures relating thereto, in which.

Figure 3:
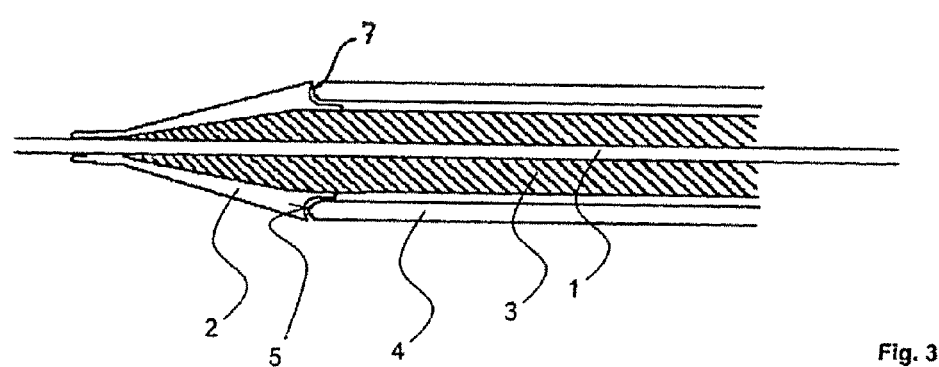
Figure 4:
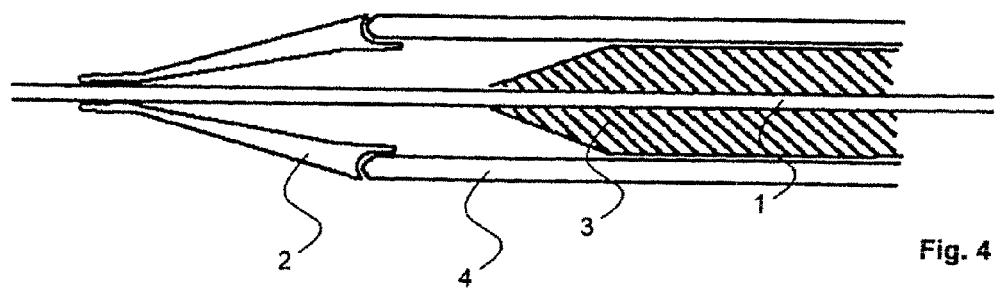
Figure 5:
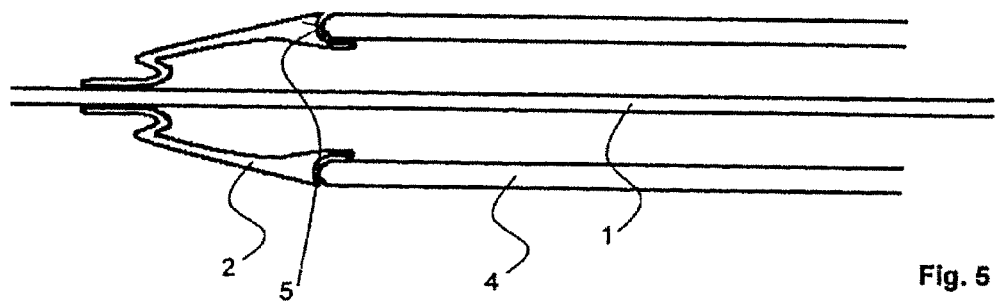
Figure 6:
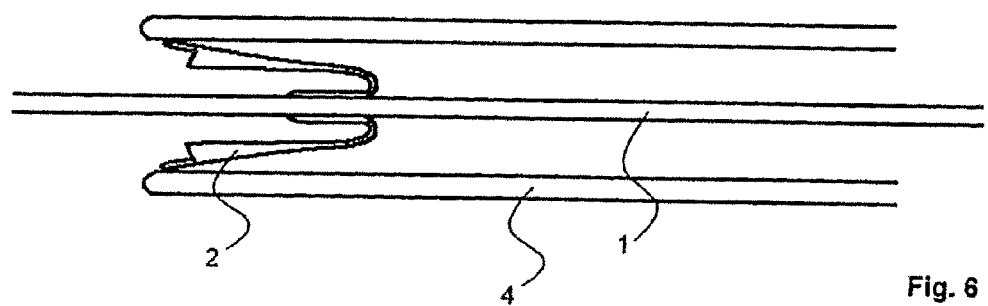
Figure 7:
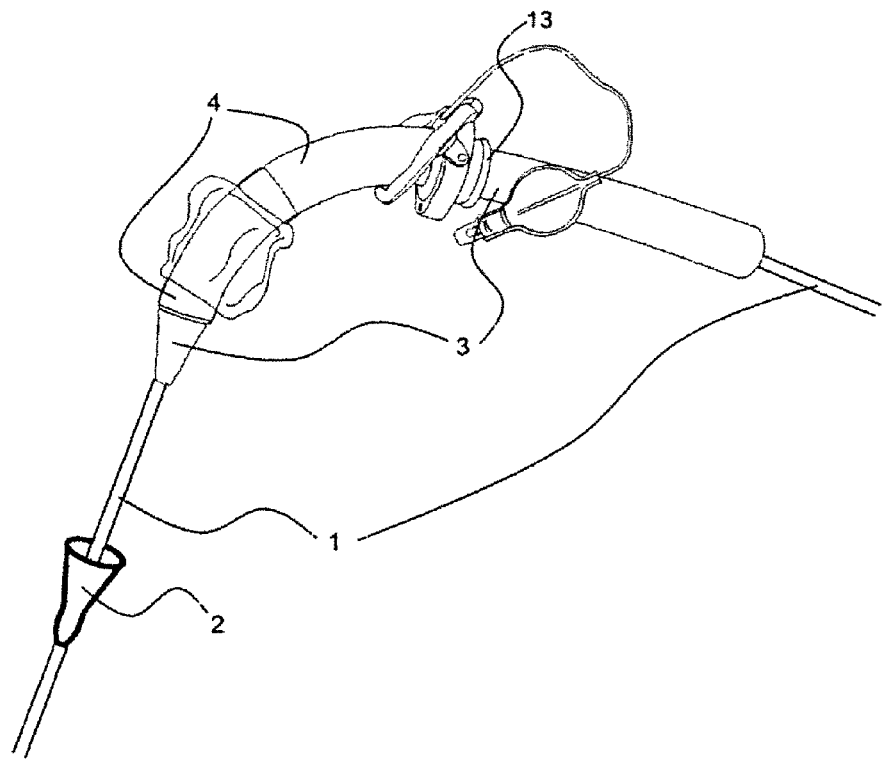
Figure 8:
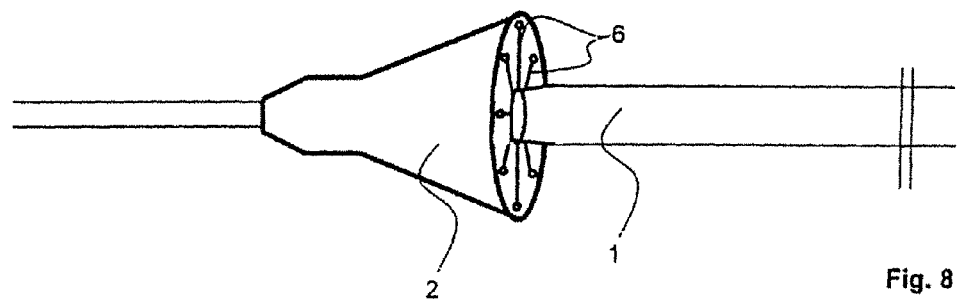

FIG. 3 shows a longitudinal section through a tracheal cannula with guide catheter, displacement body and shield in a first state, FIG. 4 shows a longitudinal section through a tracheal cannula with guide catheter, displacement body and shield, wherein the displacement body is retracted, FIG. 5 shows a longitudinal section through a tracheal cannula with guide catheter and shield in the transition from the first to the second state, FIG. 6 shows a longitudinal section through a tracheal cannula with guide catheter and shield in the second state, FIG. 7 shows a tracheal cannula into which a guide catheter with shield is pushed, and FIG. 8 shows a guide catheter with shield in a further embodiment.

Figure 1:
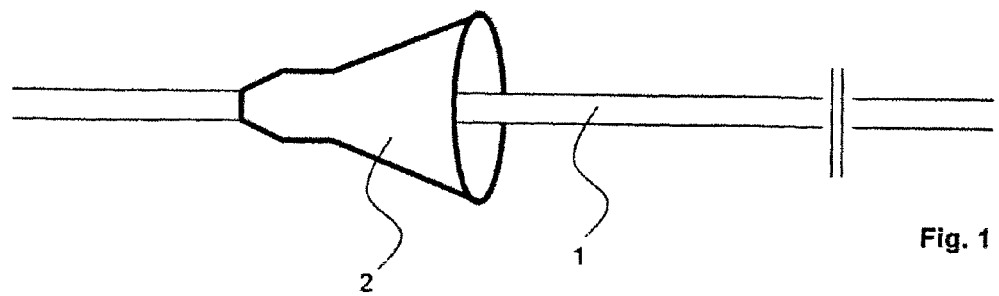
FIG. 1 shows a guide catheter with shield in a first embodiment.

FIG. 1 shows a guide catheter 1 with a first embodiment of a shield 2. The shield is in the shape of a hollow cone having substantially conical inside and outside surfaces. Shown at the distal end of the shield 2 is an attachment in the form of a hollow cylinder, which in turn has a substantially conical tip which prevents an abrupt change in calibre between the guide catheter 1 and the shield 2. The shield 2 is disposed on the guide catheter 1 at the level of the safety stopper or in place of the safety stopper which, in the known insertion aids, provides that the insertion aid cannot be pushed completely over the guide catheter 1 by error.

The safety stopper of conventional guide catheters involves a thickening of the catheter tube. If the shield in the device according to the invention is disposed in such a way that such a thickening is directly in proximal relationship with the tip of the shield, that provides that the tip of the shield is particularly stabilised and fixing of the shield is also facilitated without limiting the retractability of the catheter with the shield through the tracheal cannula.

Figure 2:
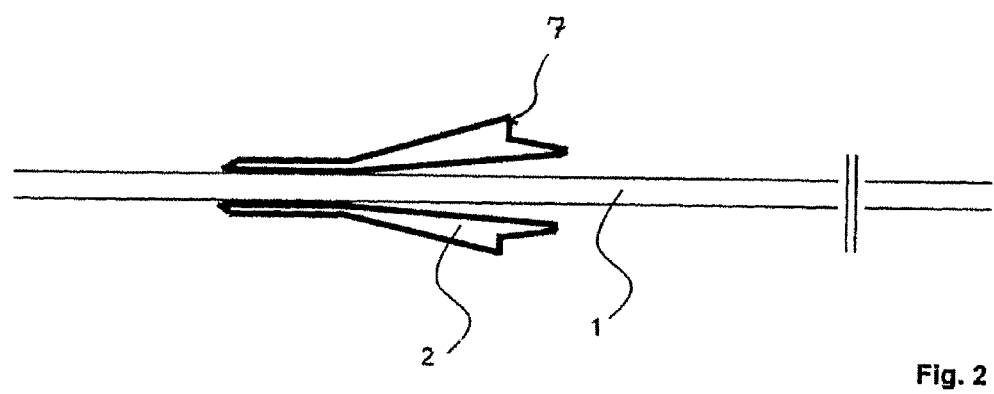
FIG. 2 shows a guide catheter with shield in a further embodiment.

FIG. 2 shows a longitudinal section through a further embodiment of a guide catheter 1 with shield 2. The shield 2 at its distal end has a thin-walled hollow-cylindrical attachment which is pointed. The attachment represents an elongated tip of the conical shield 2 and provides that there is a sufficient area between the shield 2 and the guide catheter 1 for them to be joined together by adhesive or welding. The shield illustrated here further has at its base a hollow-cylindrical attachment, the outside diameter of which is smaller than the diameter of the base of the shield and the inside diameter of which is larger than the outside diameter of the displacement body. The inside surface of the attachment represents a continuation of the inside surface of the shield 2 and the attachment tapers in the proximal direction.

FIG. 3 shows a longitudinal section of the distal end of a tracheal cannula 4, a guide catheter 1 with a further embodiment of a shield 2 and a displacement body 3. The attachment at the base of the shield 2 is disposed between the cannula tube 4 and the displacement body 3. The displacement body 3 thus fixes the shield 2 in a position in which the shield 2 compensates for the change in calibre between the guide catheter 1 and the displacement body 3 with the cannula tube 4. That also prevents the shield 2 folding over or being deformed excessively early upon introduction of the cannula 4 by means of the device according to the invention. The base of the shield 2 completely covers over the distal end face 5 of the cannula tube 4 and thereby prevents injury which can occur if that surface becomes caught on the trachea. The longitudinal section clearly shows that the displacement body 3 must have a central lumen for receiving the guide catheter 1. It is otherwise not possible for the guide catheter 1 with shield 2 and the displacement body 3 to be simultaneously disposed within the cannula 4. The displacement body can also consist solely of a conical tip, optionally with a short hollow-cylindrical attachment which is joined to the proximal side of that tip by way of a tube or hose or one or more tensile wires or threads, and in that way can be retracted from the position shown in FIG. 3.

FIG. 4 shows the distal end of a cannula 4 with a displacement body 3 and the guide catheter 1 with the shield 2 from FIG. 3. In this case the displacement body 3 is displaced slightly in the direction of the proximal end of the cannula 4 so that fixing of the shield 2 and fixing of the displacement body 3 itself within the cannula 4 is nullified. The base of the shield, depending on the respective configuration of the end face of the cannula 4 and the base surface, bearing thereagainst, of the shield, could fold inwardly and slide into the cannula, by retraction of the guide catheter 1 in the direction of the proximal end of the cannula 4.

FIG. 5 shows the cannula 4 with the guide catheter 1 and the shield 2 from FIG. 3. In this case the displacement body 3 has already been removed from the tracheal cannula. By slight retraction of the guide body 1 in the proximal direction, the shield 2 is turned over from the first state in which it bridges over the change in calibre between the cannula and the displacement body, from the tip inwardly into the second state in which the guide catheter 1 with the shield 2 can be withdrawn through the cannula 4, in which case it initially still covers the distal end face 5 of the cannula 4.

FIG. 6 shows the cannula 4 with the guide catheter 1 and the shield 2 from FIG. 3, with the shield being finally in the second state. The shield 2 was deformed until it was completely turned inside out by retraction of the guide catheter 1 in the direction of the proximal end of the cannula 4. In that case the shield can certainly also fall in folds in its base region (not shown). In that folded-over state the shield 2 can be withdrawn through the cannula 2 in the direction of the proximal end.

FIG. 7 shows how a guide catheter 1 with shield 2 in its configuration as illustrated in FIG. 1 is inserted from the distal end into a cannula 4 in which there is an insertion aid 3 as a displacement body. The displacement body is a currently available insertion aid 3 having an annular attachment 13 which prevents the insertion aid from being pushed too far in the direction of the distal end of the cannula 4.

FIG. 8 shows an embodiment of a shield 2. In this embodiment the shield is distinguished by a particularly large wall thickness which can be between 1.5 and 4 mm. The incisions 6, the depth of which can be up to 90% of the wall thickness, permit the shield to be folded over inside out. Those incisions each terminate in a respective opening of a substantially circular cross-section, which prevents the shield from tearing when it is folded over. In that case the base of the shield changes over from a flat surface into a furrowed curved shape. In addition in this embodiment the shield can comprise a compressible material so that the guide catheter 1 can be more easily retracted through a tracheal cannula, jointly with the shield 2. The guide catheter 1 in this embodiment of the shield is so designed that proximally of the shield it is of a larger outside diameter. The catheter thus performs the function of a displacement body and contributes to stabilising the shield upon insertion of the tracheal cannula into the trachea of the patient. In the folded-over state the base of the shield surrounds a catheter portion of smaller outside diameter and can thereby be sufficiently compressed or deformed for it to be withdrawn through the cannula.

For the purposes of the original disclosure it is pointed out that all features as can be seen by a man skilled in the art from the present description, the drawings and the claims, even if they are described in specific terms only in connection with certain other features, can be combined both individually and also in any combinations with others of the features or groups of features disclosed here insofar as that has not been expressly excluded or technical aspects make such combinations impossible or meaningless. A comprehensive explicit representation of all conceivable combinations of features is dispensed with here only for the sake of brevity and readability of the description.

The invention claimed is:

1. A device having a guide catheter for the introduction of a tracheal cannula into a tracheostoma, characterised in that the guide catheter has a shield which is mounted in the proximity of the distal end of the guide catheter and which shield comprises a flexible material which is substantially in the form of a distally directed conical tip, wherein the tube of the guide catheter passes through the axis of said tip to extend there beyond, with a base outside diameter which in a first state approximately corresponds to the outside diameter of the tracheal cannula and in a second state by deformation is smaller than the inside diameter of the tracheal cannula and is thus retractable through the tracheal cannula, whereby a displacement body in the form of a hollow cylinder, the outside of which is smaller than the inside diameter of the cannula and which can be pushed on over the guide catheter in the cannula is in engagement with an inside surface of the shield in the first state, which displacement body can be withdrawn from the guide catheter and cannula leaving the guide catheter and the shield in place in respect to the cannula.

2. A device according to claim 1 characterised in that the shield in the first state is substantially in the form of a hollow cone and is internally and externally conical.

3. A device according to claim 1 or claim 2 characterised in that the shield has a maximum wall thickness at the base of at most 2.5 mm, preferably at most 1.5 mm, and at least 0.4 mm, preferably at least 0.5 mm.

4. A device according to one of the preceding claims 1-2 characterised in that the base of the shield is at a spacing of at least 2 cm, better at least 5 to 14 cm, particularly preferably 7 to 10 cm from the distal end of the guide catheter.

5. A device according to one of the preceding claims 1-2 characterised in that the shield is of an axial length of at least 1 cm, preferably at least 1.5 cm and at most 6 cm, preferably at most 3 cm.

6. A device according to one of the preceding claims 1-2 characterised in that the cone angle between the shield and the longitudinal axis of the guide catheter is between 3° and 30°, preferably between 5° and 15°.

7. A device according to one of the preceding claims 1-2 characterised in that the outside diameter of the displacement body is at least 0.2 mm, preferably at least 1 mm and at most 4 mm, preferably at most 1.5 mm smaller than the inside diameter of the tracheal cannula.

8. A device according to one of the preceding claims 1-2 characterised in that the base of the shield has an attachment in the form of a hollow cylinder of an outside diameter which is adapted to the inside diameter of the cannula and which is larger than or smaller than same by a maximum of 10%, preferably by a maximum of 5%, with respect to the inside diameter, and of a wall thickness which is between 0.5 mm and 2 mm, preferably between 0.5 and 1 mm.

9. A device according claim 8 characterised in that the axial length of the attachment in the form of a hollow cylinder is between 0.3 and 5 mm, preferably between 1 and 3 mm.

10. A device according to one of the preceding claims 1-2 characterised in that the displacement body has a conical tip at its distal end.

11. A device according to one of the preceding claims 1-2 characterised in that the shield comprises a substantially elastic material.

12. A device according to one of the preceding claims 1-2 characterised in that the shield and/or the displacement body are of a substantially oval cross-section.

13. A device according to one of the preceding claims 1-2 characterised in that the displacement body is a conventional insertion aid.

14. A device according to one of the preceding claims 1-2 characterised in that the shield comprises a thermoplastic elastomer (TPE), silicone, latex or polyurethane.

15. A device according to one of the preceding claims 1-2 characterised in that the shield is provided with a hydrophilic coating.

16. A device according to one of the preceding claims 1-2 characterised in that the tip of the shield distally has an attachment in the form of a hollow cylinder.

17. A device according to one of the preceding claims 1-2 characterised in that the shield is joined to the guide catheter by adhesive or integrally by injection moulding or welding.

18. A device for introducing a tracheal cannula into a tracheostoma, comprising:
   a guide catheter having a soft tip at its distal end;
   a cannula, wherein said guide catheter is extendable through said cannula and beyond its distal end;
   a conical-shaped shield of compressible and collapsible material, said shield also having a conical-shaped interior wall, said shield being mountable on the distal end of said cannula at its base with said conical taper facing distally;
   a displacement body positionable within said cannula at the distal end thereof, said displacement body having a conical tip at its distal end positionable against the interior wall of said shield, with the taper of said displacement body abutting the taper of said shield for stabilizing said shield against deforming and folding over;
   wherein said guide catheter extends through said cannula, through said displacement body, and through said shield along the longitudinal centerline thereof, to extend beyond the distal tip of said shield.

19. The device of claim 18, wherein said shield has a cylindrical portion extending distally from the tip of said conical-shaped shield, the distal end of said cylindrical portion being conically tapered, said guide catheter extending through the longitudinal centerline of said cylindrical portion to extend the soft tip of said catheter beyond the tapered distal end of said cylindrical portion, wherein said cylindrical portion and said guide catheter portion adjacent thereto are bonded together.

20. The device of claim 18, wherein said shield is of a material which is flexible and elastic sufficiently to permit said shield to collapse and turn inside out when said displacement body is withdrawn and not stabilizing said shield, and when said shield is drawn towards the proximal end of said cannula,
   wherein the outside wall of said shield is provided with a hydrophilic coating; and
   wherein the proximal end of said shield includes a step which abuts the inside wall of said cannula distal end providing stabilization for said shield, and which collapses into the inside wall of said cannula when said shield collapses and turns inside out.

* * * * *